United States Patent [19]
Neri et al.

[11] Patent Number: 4,810,579

[45] Date of Patent: Mar. 7, 1989

[54] ORGANIC PHOSPHITES RESISTANT TO HYDROLYSIS, AND PROCESS FOR PREPARING THEM

[75] Inventors: Carlo Neri, San Donato Milanese; Nereo Nodari, Spino d'Adda; Erik Bersanetti, Milan; Giovanni Sandre, San Donato Milanese, all of Italy

[73] Assignee: Enichem Synthesis S.p.A., Palermo, Italy

[21] Appl. No.: 154,888

[22] Filed: Feb. 11, 1988

[30] Foreign Application Priority Data

Feb. 13, 1987 [IT] Italy ................. 19367 A/87

[51] Int. Cl.$^4$ ................. B05D 3/04; B05D 7/00; B32B 5/16; B32B 9/04
[52] U.S. Cl. ................. 428/405; 428/447; 427/212; 427/387
[58] Field of Search ............. 427/262, 387; 428/405, 428/447

[56] References Cited

U.S. PATENT DOCUMENTS 3,516,963 6/1970 Friedman ................. 525/452

Primary Examiner—Michael Lusignan
Attorney, Agent, or Firm—Hedman, Gibson, Costigan & Hoare

[57] ABSTRACT

Solid organic phosphites in powder form, used to endow organic polymers with stability characteristics are made resistant to hydrolysis by treating said powder phosphites with a silane containing in its molecule at least two alkoxy groups and causing the silane to hydrolyze, and the formation and deposition of a siliconic polymer on the surface of powder particles to occur.

8 Claims, No Drawings

ORGANIC PHOSPHITES RESISTANT TO HYDROLYSIS, AND PROCESS FOR PREPARING THEM

The present invention relates to solid organic phosphites resistant to hydrolysis, and to the process for preparing them.

The organic phosphites are compounds which are used in the art in order to endow the organic polymers with stability characteristics, against the oxidative degradation caused by light and/or heat, such as disclosed, e.g., in U.K. Patent No. 803,557 and U.S. Pat. No. 3,516,963.

The organic phosphites suffer from the undesired characteristic of undergoing phenomena of hydrolysis, in particular during their storage under warm and moist conditions, with the consequent loss of stabilizing activity, and danger of corrosion of the equipment used for processing the organic polymers incorporating said hydrolysed phosphites.

Therefore, it is usual in the art to stabilize the organic phosphites by means of the addition of such organic bases as: hexamethylenetetramine, triisopropanolamine, stearyldimethylamine and still others, which act by buffering the acidity which is formed during the hydrolysis, and therefore slow down the hydrolysis rate.

However, this operating way does not make it possible satisfactory results to be achieved, in particular in case of the organic phosphites derived from pentaerythritol, whose sensitivity to hydrolysis remains high even in the presence of an organic base.

Therefore, the purpose of the present invention is to overcome this prior state of the art and endow the solid organic phosphites with exceptionally high characteristics of resistance to hydrolysis.

In particular, according to the present invention, the solid organic phosphites in powder form, with a particle size of from 50 μm to 1 mm, are treated with a silane containing at least two alkoxy groups in its molecule, and the hydrolysis of the silane, and the formation and deposition of a siliconic polymer on the surface of the particles of the powder are caused.

Advantageously, for such a purpose an amount of silane of from 0.1 to 10% by weight relatively to the solid phosphite, and, preferably, an amount of the order of from 0.5 to 2% by weight, is used.

The present Applicant has unexpectedly found that such a treatment gives the organic phosphites an exceptionally high resistence to hydrolysis, with in no way affecting the organic polymer stabilizing activity of the same phosphites.

The organic phosphites which can be made resistant to hydrolysis according to the present invention, are the solid phosphites which are known from the art owing to their ability to stabilize the organic polymers.

A class of these organic phosphites may be defined by means of the general formula:

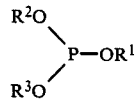

wherein: $R^1$, $R^2$ and $R^3$ represent either equal or different hydrocarbyl radicals, which can be either substituted or non-substituted alkyl, cycloalkyl, aryl, alkaryl or aralkyl radicals.

In particular, trialkyl phosphites, dialkyl monophenyl phosphites, diphenyl monoalkyl phosphites and triphenyl phosphites, possibly bearing hydrocarbyl substituents on the benzene ring, are known and used in the art.

Specific examples of such organic phosphites are: diphenyl 2-ethylhexyl phosphite, triphenyl phosphite, tris(2,5-di-tert.-butyl-phenyl)phosphite, tris(2-tert.-butylphenyl)phosphite, tris(2-phenylphenyl)phosphite, tris[2-(1,1-dimethylpropyl)phenyl]phosphite, tris(2-cyclohexylphenyl)phosphite, tris(2-tert.-butyl-4-phenylphenyl)phosphite, tris(2-tert.-butyl-4-methylphenyl)phosphite, tris(2,4-di-tert.-amylphenyl)phosphite and tris(2,4-di-tert.-butylphenyl)phosphite.

Another class of organic phosphites which can be stabilized according to the present invention is definable by means of the general formula:

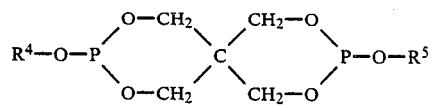

wherein: $R^4$ and $R^5$ radicals, equal to, or different from, each other, represent hydrocarbyl radicals, which can be either substituted or non-substituted alkyl, cycloalkyl, aryl, alkaryl or aralkyl radicals.

Specific examples of such organic phosphites are: bis(2,4-di-tert.-butylphenyl)pentaerythritol diphosphite and distearyl pentaerythritol diphosphite.

The silanes which are used in the process according to the present invention are those which contain in their molecule at least two alkoxy, and preferably methoxy, groups, which are normally used in the art as "bonding agents" for fillers in polymers, and which are capable of hydrolysing in the presence of water and of crosslinking originating polymers of siliconic nature.

Specific examples of such silanes are: γ-aminopropyl trimethoxy silane; γ-aminopropyl triethoxy silane; γ-aminopropyl methyldiethoxy silane; N-β-aminoethyl-γ-aminopropyl trimethoxy silane; N-β-aminoethyl-γ-aminopropyl methyldimethoxy silane; 4,5-dihydro-1-[3-(triethoxysilyl)propyl]imidazole; γ-mercaptopropyl trimethoxy silane; γ-mercaptopropyl trimethoxy silane; γ-mercaptopropyl methyldimethoxy silane; γ-glycidyloxypropyl trimethoxy silane; γ-methacryloxypropyl trimethoxysilane; γ-chloropropyl trimethoxy silane; γ-chloropropyl triethoxy silane; γ-chloropropyl methyldimethoxy silane; vinyl trimethoxy silane; vinyl triethoxy silane; and vinyl tris(β-methoxyethoxy)silane.

According to a form of practical embodiment of the process of the present invention, the organic phosphite, in a powder form, is suspended in an inert solvent wherein the same phosphite is insoluble, or substantially insoluble, and which contains the silane and an amount of water at least equal to the required amount for hydrolysing the silane. Examples of such solvents are liquid aliphatic hydrocarbons, such as hexane and heptane.

The suspension is kept stirred, by operating at room temperature (20°-25° C.), for a time of from 10 to 120 minutes. The solvent is the evaporated off under reduced pressure and a powder is recovered, which is heated to a temperature preferably comprised within the range of from 100° to 140° C., by operating under a reduced pressure and for a time of from 10 minutes to 12 hours, such as to remove any possible solvent traces, and cause the siliconic polymer to form on the surface of the particles of the organic phosphite.

According to a further form of practical embodiment, on the organic phosphite powder the silane, preferably diluted in an inert organic solvent, containing a water amount at least necessary to cause the hydrolysis of the same silane, is sprayed. These operations are advantageously carried out at room temperature (20°-25° C.), and the so-treated powder of the organic phosphite is then heated under a reduced pressure, in a way similar to as above disclosed with regard to the first form of practical embodiment.

When the treatment process is carried out under the above indicated conditions, the treated organic phosphite will advantageously show a melting point higher than approximately 100° C.

Particularly good results are obtained by applying the process of the present invention to the stabilization of the following phosphites: bis(2,4-di-tert.-butylphenyl)-pentaerythritol diphosphite; di-stearyl pentaerythritol diphosphite; and tris(2,4-di-tert.-butylphenyl)phosphite.

The preferred silane for the process of the present invention is vinyl triethoxy silane.

By means of the process of the present invention organic phosphites are obtained, in the form of an anhydrous and free-flowing powder, having an exceptional resistance to hydrolysis, and which maintain unchanged their activity in the stabilization of the organic polymers.

The following experimental examples are illustrative and not limitative of the purview of the present invention.

EXAMPLE 1

200 g of bis(2,4-di-tert.-butylphenyl) pentaerythritol diphosphite, freshly crystallized (melting point 165° C.) in the form of a powder with a particle size of the order of 250 μm, is suspended in 250 ml of hexane, and to the suspension 4 g of vinyl triethoxy silane and 0.5 g of water are added, by operating at room temperature (20°-25° C.).

The suspension is then vigorously stirred at room temperature for one hour, and at the end of this time period, the solvent is evaporated off by operating under a reduced pressure of 150 $mm_{Hg}$ and at a temperature of approximately 80° C.

The resulting solid product is maintained in an oven, heated at 120° C., for 6 hours, and under a reduced pressure (approximately 20 $mm_{Hg}$).

202 g is recovered of a product in the form of a white, dry powder, which is submitted to the test for stability to hydrolysis.

EXAMPLE 2

The process is run as disclosed in Example 1, with distearyl pentaerythritol diphosphite being used, in the form of a powder with a particle size of the order of 150 μm.

The resulting powder product is submitted to the test for stability to hydrolysis.

EXAMPLE 3

The process is run as in Example 1, with tris-(2,4-di-tert.-butylphenyl)phosphite (melting point 183° C.) being used, in the form of a powder with a particle size of the order of 400 μm.

The resulting powder product is submitted to the test for stability to hydrolysis.

EXAMPLE 4

10 Grams of the powder product obtained in Example 1 is charged to each one from 6 dishes having a diameter of 10 cm. The dishes are then placed inside an oven maintained at the controlled temperature of 50° C., and containing on its floor a steel tank filled with water. A hygrometer provided inside the oven reads a level of relative humidity of 96-98%.

The dishes are removed from the oven respectively after 1, 2, 3, 4, 5 and 20 hours from the beginning of the test, and the contents of the dish are submtted to gas-chromatographic analysis in order to determine the content of free 2,4-di-tert.-butylphenol.

The results of this test are reported in Table 1, under (A), wherein the % values reported as a function of the various times relate to free 2,4-di-tert.-butylphenol as a percentage of total 2,4-di-tert.-butylphenol, i.e., of the amount of 2,4-di-tert.-butylphenol which would be released in case of a complete hydrolysis.

In Table 1, for comparative purposes, under (B) the results are reported, which were obtained with bis(2,4-di-tert.-butylphenyl) pentaerythritol diphosphite as such (i.e., not treated), and under (C) the results are shown, which were obtained by using the commercial product ULTRANOX® 626, viz., a commercial bis(2,4-di-tert.-butylphenyl) pentaerythritol diphosphite which, according to as declared by the Manufacturer, is stabilized with approximately 1% by weight of triisopropanolamine.

TABLE 1

| Product | Hydrolysis % | | | | | |
|---|---|---|---|---|---|---|
| | 1 hour | 2 hours | 3 hours | 4 hours | 5 hours | 20 hours |
| (A) | 1% | 5% | 8% | 12% | 18% | 68% |
| (B) | 15% | 40% | 80% | 100% | — | — |
| (C) | 6% | 28% | 46% | 72% | 100% | — |

EXAMPLE 5

The process is carried out as in Example 4, by submitting to the test for stability to hydrolysis the distearyl pentaerythritol diphosphite obtained in Example 2. In this case, the amount of stearyl alcohol released owing to the effect of the hydrolysis, is determined by gas-chromatographic analysis.

The results are reported in Table 2, under (A). In the same Table, for comparative purposes, under (B) the results are reported, which were obtained with distearyl pentaerythritol diphosphite as such (i.e., not treated), and under (C) the results are shown, which were obtained by using the commercial product WESTON® 618, viz., a commercial distearyl pentaerythritol diphosphite which, according to as declared by the Manufacturer, is stabilized with approximately 1% by weight of triisopropanolamine.

TABLE 2

| Product | Hydrolysis % | | | | | |
|---|---|---|---|---|---|---|
| | 1 hour | 2 hours | 3 hours | 4 hours | 5 hours | 20 hours |
| (A) | 2% | 6% | 9% | 14% | 20% | 88% |
| (B) | 18% | 45% | 87% | 100% | — | — |
| (C) | 8% | 27% | 48% | 80% | 100% | — |

EXAMPLE 6

The process is carried out as in Example 4, by submitting to the test for stability to hydrolysis the tris(2,4-di-tert.butylphenyl)phosphite obtained in Example 3. In this case, the amount of 2,4-di-tert.-butyl phenol released due to the effect of the hydrolysis, is determined by gas-chromatographic analysis.

The results are reported in Table 3, under (A). In the same Table, for comparative purposes, under (B) the results are reported, which were obtained with the commercial product IRGAFOS ® 168, i.e., a commercial tris(2,4-di-tert.-butylphenyl) phosphite which, according to as specified by the Manufacturer, does not contain any stabilizers to hydrolysis.

TABLE 3

| Product | Hydrolysis % | | | | | |
|---|---|---|---|---|---|---|
| | 1 hour | 2 hours | 3 hours | 4 hours | 5 hours | 20 hours |
| (A) | 0.1% | 0.2% | 0.4% | 0.6% | 0.8% | 3.5% |
| (B) | 0.2% | 0.5% | 1% | 1.5% | 2% | 12% |

We claim:

1. Process for endowing a solid organic phosphite in powder form with stability to hydrolysis, characterized in that the powder of said phosphite, having a particle size of from 50 μm to 1 mm, is treated with an amount of from 0.1 to 10% by weight, relatively to the organic phosphite, of a silane containing at least two alkoxy groups in its molecule, and the hydrolysis of the silane, and the formation and deposition of a siliconic polymer on the surface of the particles of the powder are caused.

2. Process according to claim 1, characterized in that the phosphite powder is suspended in an inert organic solvent which contains the silane and a water amount at least equal to the required amount for hydrolysing the silane, the suspension is stirred at room temperature (20°–25° C.) for a time of from 10 to 120 minutes, the organic solvent is evaporated off, and the so obtained powder is treated at a temperature of from 100° to 140° C. for a time of from 10 minutes to 12 hours, by operating under a reduced pressure.

3. Process according to claim 2, characterized in that the inert organic solvent is selected from hexane and heptane.

4. Process according to claim 1, characterized in that on the phosphite powder the silane diluted in an inert organic solvent containing a water amount at least equal to the water amount required for hydrolysing the same silane is sprayed, with the process being carried out at room temperature, and the so-treated powder is maintained at a temperature of from 100° to 140° C. for a time of from 30 minutes to 12 hours under a reduced pressure.

5. Process according to claim 1, characterized in that the organic phosphite has a melting point higher than approximately 100° C.

6. Process according to claim 5, characterized in that said organic phosphite is selected from bis(2,4-di-tert.-butylphenyl)pentaerythritol diphosphite; distearylpentaerythritol diphosphite and tris(2,4-di-tert.-butylphenyl) phosphite.

7. Process according to claim 1, characterized in that said silane is vinyl triethoxy silane.

8. Organic phosphites stabilized to hydrolysis, obtained according to the process of any one of claims 1 to 7.

* * * * *